United States Patent [19]

Baumann et al.

[11] Patent Number: 5,047,376
[45] Date of Patent: Sep. 10, 1991

[54] CURING COMBINATION FOR CATIONICALLY POLYMERIZABLE MATERIALS

[75] Inventors: Dieter Baumann, Möhlin; Kurt Meier, Binningen; Werner Margotte, Lupsingen; Beat Müller, Marly, all of Switzerland

[73] Assignee: Ciba-Geigy Corporation, Ardsley, N.Y.

[21] Appl. No.: 386,526

[22] Filed: Jul. 27, 1989

[30] Foreign Application Priority Data

Aug. 4, 1988 [CH] Switzerland ............ 2959/88

[51] Int. Cl.$^5$ ............................................. G03C 1/68
[52] U.S. Cl. ............................................. 502/5; 502/52; 502/53; 502/55; 528/89; 528/90; 528/91; 528/92; 528/403
[58] Field of Search ............ 502/5, 52, 53, 55; 528/89, 90, 91, 92, 403

[56] References Cited

U.S. PATENT DOCUMENTS 4,740,577  4/1988  DeVoe et al. .................. 528/51

FOREIGN PATENT DOCUMENTS 109851   5/1984  European Pat. Off. .
837966   6/1984  South Africa .
843733   1/1985  South Africa .
850973   9/1985  South Africa .

Primary Examiner—Maurice J. Welsh
Assistant Examiner—Rachel F. Johnson
Attorney, Agent, or Firm—Luther A. R. Hall

[57] ABSTRACT

The present invention relates to activated curing combinations for organic cationically polymerizable materials. The curing combinations are obtainable by activating a solution or a dispersion of an iron/arene salt and a polycarboxylic acid, an anhydride based on a polycarboxylic acid, or a polyisocyanate by heating or by irradiation with actinic radiation. The curable compositions containing these activated curing combinations can be used as sheathing or encapsulating materials for electronic components.

18 Claims, No Drawings

CURING COMBINATION FOR CATIONICALLY POLYMERIZABLE MATERIALS

The present invention relates to novel compositions of matter which can be used as curing agents for cationically polymerizable materials, to cationically polymerizable materials containing these curing agents, to a process for the curing of said materials and to the use of the novel compositions of matter as curing agents for cationically polymerizable materials.

The use of metallocene complexes as curing agents for cationically polymerizable materials and/or materials polymerizable by free radicals is known per se.

EP-A 94,915 and 109,851 have described curable compositions containing cationically polymerizable materials, preferably epoxy resins, and metallocene salts as curing agents. EP-A 94,915 also discloses activated compositions obtained by irradiation of the curable compositions by means of actinic radiation and curable at lower temperatures compared with direct curing.

EP-A 126,712 discloses combinations of cationically polymerizable materials and/or materials polymerizable by free radicals, containing an iron/arene complex salt and an oxidizing agent.

EP-A 152,377 describes combinations of cationically polymerizable material and/or material polymerizable by free radicals, selected iron/arene complex salts, sensitizers and, if appropriate, oxidizing agents.

Furthermore, U.S. Pat. No. 4,740,577 discloses polymerizable compositions containing a polyurethane precursor and a salt of an organic complex cation as curing agent.

The common feature of all these disclosed compositions is that the organometallic complex salts, after mixing into the material to be polymerized, are activated by irradiation with actinic radiation before the heat curing, as a result of which, depending upon material and irradiation conditions, partial polymerization can take place, and are then heat-cured, or that the direct heat curing takes place at high temperatures, for example near the decomposition temperature of the complex salt.

For a number of applications, for example for use in encapsulating and sheathing processes in the production of integrated circuits or as rapidly-curing one-component adhesives, curable compositions which combine properties which are opposite per se and therefore difficult to achieve, such as sufficient shelf life of the uncured composition and a fairly high curing rate at relatively low temperatures, are desired.

There is still a general demand for curable compositions which meet this extremely desirable range of properties.

Curing combinations for cationically polymerizable organic materials have now been found, by means of which rapid gelling at low temperatures compared with previously known compositions is possible and for which only short post-curing times or low post-curing temperatures are required. At the same time, these curable compositions have a long shelf life, so that their use in the abovementioned processes leads to advantages during processing.

Furthermore, in the case of the novel curing combinations, activation of the curable compositions by irradiation before the curing step can be omitted, so that the processing is generally simplified, in particular in systems having a high filler content or in the curing of thick layers, in which irradiation of the entire curable composition may be problematical.

The present invention relates to a composition of matter obtainable by

A) dissolving or dispersing a component i) in a component ii), component i) being a compound of the formula I $$[(R^1)(R^2 Fe^{II})_a]^{+na} n a X^-  \quad (I)$$

and component ii) being selected from the group consisting of a polycarboxylic acid, an anhydride, based on a polycarboxylic acid, in particular a dicarboxylic anhydride or a polyisocyanate, in which, in formula I, $R^1$ is a π-arene, $R^2$ is a π-arene or an anion of a π-arene, a and n, independently of one another, are 1 or 2, and X is an anion $[LQ_m]^-$ or an anion of an unfluorinated, partially fluorinated or perfluorinated aliphatic, cycloaliphatic, aromatic or araliphatic carboxylic acid or sulfonic acid, in which L is selected from the group consisting of B, P, As, Sb and Bi, Q is a halogen atom and m corresponds to the valency of L increased by one, and B) activating said solution or dispersion containing components i) and ii) by irradiation with actinic radiation or by heating, so that component i) is virtually no longer detectable in said solution or dispersion.

Very generally, a π-arene $R^1$ or $R^2$ is understood to mean a unidentate or bidentate neutral aromatic π ligand which in each case contributes 6 π electrons to the valence shell of $Fe^{II}$ and thus forms a complex bond with the valence shell of $Fe^{II}$ via its aromatic π system.

As a rule, these ligands are nonbasic heterocyclic-aromatic or in particular carbocyclic-aromatic hydrocarbons which are mono- or poly-nuclear and, in the case of polynuclear radicals, can be nonfused or fused.

These ligands can be unsubstituted or they can be substituted by one or more nonbasic radicals.

Preferred π-arenes $R^1$ or $R^2$ are carbocyclic-aromatic hydrocarbons having 6–24 C atoms, in particular 6–12 C atoms, in the aromatic ring, or heterocyclic-aromatic hydrocarbons having 4–11 C atoms and 1 or 2 O atoms or S atoms in the aromatic ring, it being possible for these ligands to be mono- or polysubstituted by identical or different monovalent radicals, such as halogen atoms, preferably chlorine or bromine atoms, alkyl, preferably $C_1$–$C_8$alkyl, alkoxy, preferably $C_1$–$C_8$alkoxy, alkylthio, preferably $C_1$–$C_8$alkylthio, or by phenyl radicals.

Nonfused, polynuclear π-arenes can be linked directly or via bridge members, such as —CH$_2$—, —C(CH$_3$)$_2$—, —CH=CH—, —O—, —S—, —SO$_2$—or —CO—.

The alkyl, alkoxy or alkylthio groups can be straight-chain or branched.

Examples of typical alkyl groups are methyl, ethyl, n-propyl, isopropyl, n-butyl, isobutyl, n-pentyl, n-hexyl, n-heptyl, n-octyl, 2-ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl and n-eicosyl.

Examples of typical alkoxy groups are methoxy, ethoxy, n-propoxy, isopropoxy, n-butoxy, isobutoxy, n-pentoxy, n-hexoxy, n-heptoxy, n-octoxy, 2-ethylhexoxy, n-nonoxy and n-decoxy.

Examples of typical alkylthio groups are methylthio, ethylthio, n-propylthio, isopropylthio, n-butylthio, isobutylthio, n-pentylthio, n-hexylthio, n-heptylthio, n-octylthio, 2-ethylhexylthio, n-nonylthio and n-decylthio.

Alkyl or alkoxy groups having 1–4 C atoms are preferred substituents.

Examples of suitable $\pi$-arenes $R^1$ and $R^2$ are benzene, toluene, xylenes, ethylbenzene, cumene, methoxybenzene, ethoxybenzene, dimethoxybenzene, p-chlorotoluene, m-chlorotoluene, chlorobenzene, bromobenzene, dichlorobenzene, trimethylbenzene, hexamethylbenzene, trimethoxybenzene, naphthalene, 1,2-dihydronaphthalene, 1,2,3,4-tetrahydronaphthalene, methylnaphthalene, methoxynaphthalene, ethoxynaphthalene, chloronaphthalene, bromonaphthalene, biphenyl, stilbene, indene, 4,4'-dimethylbiphenyl, fluorene, phenanthrene, anthracene, 9,10-dihydroanthracene, triphenyl, pyrene, perylene, naphthacene, chrysene, coronene, thiophene, furan, chromene, xanthene, xanthone, thioxanthone, benzofuran, benzothiophene, naphthothiophene, thianthrene, diphenylene oxide or diphenylene sulfide.

In general, an anion of a $\pi$-arene $R^2$ is understood to mean an anionic aromatic unidentate $\pi$ ligand which in each case contributes 6 $\pi$ electrons to the valence shell of $Fe^{II}$ and thus forms a complex bond with the valence shell of $Fe^{II}$ via its aromatic $\pi$ system.

These ligands can be unsubstituted or they can be substituted by one or more nonbasic radicals.

Preferred anions of a $\pi$-arene $R^2$ are the indenyl anion and, in particular, the cyclopentadienyl anion, it being possible for these ligands to be mono- or polysubstituted by the abovementioned radicals.

Examples of preferred anions of a $\pi$-arene are anions of methyl-, ethyl-, n-propyl- and n-butylcyclopentadiene, the anion of dimethylcyclopentadiene and, in particular, the anion of unsubstituted cyclopentadiene.

In the case where a is 2, $R^2$ is preferably in each case a substituted or unsubstituted indenyl anion or, in particular, a substituted or unsubstituted cyclopentadienyl anion and $R^1$ is a bidentate $\pi$ligand which contributes 6 $\pi$ electrons to each $Fe^{II}$; in this case n is 1.

The index a is preferably 1.

The index n is preferably 1.

$X^-$ is preferably an anion $[LQ_m]^-$ or an anion of a partially fluorinated or perfluorinated aliphatic or aromatic sulfonic acid.

Q is preferably fluorine and L is preferably P, As, Sb or Bi.

Examples of particularly preferred anions $X^-$ are $PF_6^-$, $AsF_6^-$, $SbF_6^-$, $BiF_6^-$, and anions of perfluoroaliphatic or perfluoroaromatic sulfonic acids, in par;ticular $CF_3-SO_3^-$, $C_3F_7-SO_3^-$, $C_4F_9-SO_3^-$, $C_6F_{13}-SO_3^-$, $C_8F_{17}-SO_3^-$, $C_6F_5-SO_3^-$ and $CF_3-C_6F_4-SO_3^-$.

The polycarboxylic acids which can be used as component ii) can be in general aliphatic, cycloaliphatic, aromatic or araliphatic compounds having at least two carboxyl groups, in particular having two carboxyl groups.

Examples of polycarboxylic acids are saturated aliphatic dicarboxylic acids, such as oxalic acid, malonic acid, succinic acid, $\alpha$-methylsuccinic acid, glutaric acid, adipic acid, pimelic acid, azelaic acid, sebacic acid or dimerized linolic acid; or unsaturated aliphatic dicarboxylic acids, such as maleic acid, mesaconic acid, citraconic acid, glutaconic acid or itaconic acid; or cycloaliphatic dicarboxylic acids, such as hexahydrophthalic acid, hexahydroisophthalic acid or hexahydroterephthalic acid, or tetrahydrophthalic acid, tetrahydroisophthalic acid or tetrahydroterephthalic acid, or 4-methyltetrahydro-phthalic acid, 4-methylhexahydrophthalic acid or endo-methylenetetra-hydrophthalic acid; or aromatic dicarboxylic acids, such as phthalic acid, isophthalic acid or terephthalic acid.

Examples of tricarboxylic acids and higher carboxylic acids are, in particular, aromatic tri- or tetracarboxylic acids, such as trimellitic acid, trimesic acid, pyromellitic acid or benzophenonetetracarboxylic acid, and dimerized or trimerized fatty acids, such as are commercially available, for example, under the name Pripol ®.

The anhydrides of component ii) are derived from organic polycarboxylic acids, in particular from dicarboxylic acids. Examples are the anhydrides of the polycarboxylic acids listed above.

In the case where component ii) is a polyisocyanate, in general any aliphatic, cycloaliphatic, aromatic or araliphatic compound can be used having at least two isocyanate groups or blocked isocyanate groups which can be unblocked by heating and which can be dissolved or dispersed in component i).

Polyisocyanates are particularly preferred as components ii), since by using these initiator compositions it is, as a rule, possible to prepare cured products having particularly high glass transition temperatures, which furthermore only show a small degree of network decomposition upon thermal stress.

Examples of preferred polyisocyanates are 2,6-diisocyanatotoluene, 2,4-diisocyanatotoluene and technical grade mixtures thereof with 2,6-diisocyanatotoluene, 1,5-diisocyanatonaphthalene, 4,4'-diisocyanatodiphenylmethane and technical grade mixtures of different diisocyanatodiphenylmethanes (for example the 4,4'- and 2,4'-isomers), urethanized 4,4'-diisocyanatodiphenyl-methane, carbodiimidized 4,4'-diisocyanatodiphenylmethane, the uretdione of 2,4-diisocyanatotoluene, triisocyanatotriphenylmethane, the adduct from diisocyanatotoluene and trimethylolpropane, the trimer from diisocyanatotoluene, diisocyanato-m-xylylene, N,N'-di(4-methyl-3-isocyanatophenyl)urea, mixed trimerization products from diisocyanato- toluene and 1,6-diisocyanatohexamethylene, 1,6-diisocyanatohexane, 3,5,5-trimethyl-1-isocyanatomethylcyclohexane (isophorone diisocyanate), N,N',N''-tri(6-isocyanatohexyl)biuret, 2,2,4-trimethyl-1,6-diisocyanoto-hexane, 1-methyl-2,4-diisocyanatocyclohexane, dimeryl diisocyanate, 4,4'-diisocyanatodicyclohexylmethane, trimeric isophorone diisocyanate, trimeric hexane diisocyanate and methyl 2,6-diisocyanatohexanoate.

Preferred polyisocyanates have three or, in particular, two isocyanate groups and 6 to 20 carbon atoms. Very particular preference is given to aromatic diisocyanates, in particular 4,4'-diisocyanatodiphenylmethane and technical grade mixtures of various diisocyanatodiphenylmethanes, or cycloaliphatic diisocyanates, in particular isophorone diisocyanate.

Anhydrides of polycarboxylic acids or mixtures of anhydrides of polycarboxylic acids are also particularly preferred as component ii).

Particularly preferred anhydrides of polycarboxylic acids are liquid at temperatures below 50° C., in particular below 30° C. These can also be liquid mixtures of different anhydrides of polycarboxylic acids.

As a rule, the starting mixture is prepared by simply mixing components i) and ii), if appropriate with heating, thus forming a solution of i) in ii). In the case where the starting components are not or only partially soluble in one another, it is also possible to work with a dispersion of component i) in ii). To this end, the mixture can be melted in a manner known per se and treated with ultrasound.

Preferably, components i) and ii) and their amounts are selected such that it is possible to prepare a solution from these components.

The structure of the activated curing component according to the invention cannot be stated with certainty. As a result of activation by heating or irradiation with actinic radiation, component i) undergoes a reaction in the starting mixture. This can be monitored and checked, for example, with the help of chromatography. Thus, after the activation, component i), for example, can no longer be separated off from the activated curing mixture by means of thin-layer or column chromatography. The activation is therefore carried out under conditions in which a virtually complete reaction of component i) of the starting mixture takes place.

The solution or dispersion of components i) and ii) can, if desired, additionally contain a sensitizer for the compound of the formula I. Examples of suitable sensitizers are polycyclic hydrocarbons, acetophenones or benzophenones, phthalimide thioethers and thioxanthones. Further examples of suitable sensitizers can be found in EP-A 152,377. The amount of sensitizer is usually 0–10 % by weight, relative to the amount of component i).

The activation by means of actinic radiation is carried out by irradiating the solution or dispersion containing components i) and ii), as a rule in the wavelength region in which the complex of the formula I and/or any sensitizer present show absorption. Depending on ligand $R^1$ or on the sensitizer, this range is usually between about 200 and 600 nm in the electromagnetic spectrum. Light sources which are customary per se, such as xenon or argon lamps, tungsten lamps or, in particular, mercury lamps can be used for the irradiation.

The irradiation time is mainly dependent on the process parameters, such as intensity, wavelength and irradiation temperature. The optimum activation conditions can be determined by one skilled in the art on the basis of routine tests.

The activation by means of irradiation can be shortened by heating. Conventional temperatures are in the range from 30°–180° C.

Moreover, the activation can be carried out solely by heating. To this end, the solution or dispersion of components i) and ii) is heated until a reaction of the complex of the formula I takes place. In this case, too, the temperature level and activation time are mainly determined by the type of complex of the formula I. To achieve short reaction times, the solution should be heated up to about the decomposition temperature of the complex of the formula I.

When the starting mixture is prepared, virtually any ratio of the amounts can be chosen, component i) usually being present in less than an equimolar amount. The ratios of the amounts of the components chosen depend on the desired rate of the curing reaction. In general, the higher the amount of component i) in the starting mixture, the higher the rate. The weight ratios of component i) and component ii) in the starting mixture are, as a rule, 0.2:100 to 1:1, preferably 0.5:100 to 5:100.

In a preferred embodiment, the invention relates to a composition of matter obtainable by A) dissolving component i) in a combination of component ii) with a further component iii) and B) activating this solution in the manner defined above, in which component i) is as defined above, component ii) is an anhydride of a polycarboxylic acid, in particular an anhydride of a dicarboxylic acid, and component iii) is a polycarboxylic acid or a carboxyl-terminated adduct of a polycarboxylic acid or one of its ester-forming derivatives to an at least dihydric alcohol and/or an at least dihydric phenol.

In this case, the weight ratios of components i):ii)+iii) in the starting solution are, as a rule, 0.2:100 to 1:1, preferably 0.5:100 to 5:100, and the weight ratio of component ii) to iii) is preferably 100:1 to 100:20.

Activated curing combinations of components i), ii) and iii) are in general distinguished by a particularly high activity.

Very generally, aliphatic, cycloaliphatic, aromatic or araliphatic compounds having at least two carboxyl groups, in particular having two carboxyl groups, can be used as polycarboxylic acids iii) or as components for the formation of the carboxyl-terminated adducts iii).

Examples of these polycarboxylic acids have already been mentioned above. These polycarboxylic acids can be used as such or they are used for masking the corresponding alcohol components. In addition to carboxylic acids, their ester-forming derivatives, such as anhydrides, acid chlorides or esters, can also be used for the masking.

Possible alcohol components include aliphatic diols, such as alkylenediols, for example ethylene glycol, propane-1,2-diol, propane-1,3-diol, butane-1,4-diol, pentane-1,5-diol, neopentylglycol (2,2-dimethylpropanediol), hexane-1,6-diol, octane-1,8-diol, decane-1,10-diol or dodecane-1,12-diol; or polyhydric alcohols, such as 1,1,1-trimethylolethane, 1,1,1-trimethylolpropane, glycerol or pentaerythritol; or cycloaliphatic diols, such as 1,3- or 1,4-dihydroxycyclohexane, 1,4-cyclohexanedimethanol, bis(4-hydroxycyclohexyl)methane or 2,2-bis(4-hydroxycyclohexyl)propane; or bisphenols, such as resorcinol, hydroquinone, bis(4-hydroxyphenyl)-methane, bis(4-hydroxyphenyl) ether or 2,2-bis(4-hydroxyphenyl)propane.

In addition to these lower-molecular-weight alcohols or phenols, it is also quite possible to use hydroxyl-terminated prepolymers. These compounds are known per se to one skilled in the art. Examples of these are hydroxyl-terminated polyesters, such as polycaprolactone, and in particular polyethers, such as polyalkylene ether polyols, which can be obtained by ionic polymerization, copolymerization or block copolymerization of alkylene oxides, such as ethylene oxide, propylene oxide or butylene oxide, in the absence or presence of di- or polyfunctional alcohols.

The alcohol components are masked by using the polycarboxylic acid or its ester-forming derivatives in excess, so that all alcohol groups are masked. In this reaction, unreacted acid components may very well still remain. The preparation of these carboxyl-terminated components is known per se to one skilled in the art and can be carried out, for example, by condensation in the melt or by condensation in solution by heating the reaction components.

Compounds which are preferably used as component i) for preparing the activated compositions of matter according to the invention are those of the formula I in which a and n are 1, $R^1$ is a benzene or naphthalene radical which is unsubstituted or mono— or disubstituted by $C_1$-$C_4$alkyl or $C_1$-$C_4$alkoxy or is a stilbene radical, $R^2$ is an unsubstituted cyclopentadienyl anion and $X^-$ is an anion selected from the group consisting of $PF_6^-$, $AsF_6^-$, $SbF_6^-$, $BiF_6^-$, and of anions of perfluoro- aliphatic or perfluoroaromatic sulfonic acids, in particular $CF_3-SO_3^-$, $C_2F_5-SO_3^-$, $C_3F_7-SO_3^-$, $C_4F_9-SO_3^-$, $C_6F_{13}-SO_3^-$, $C_8F_{17}-SO_3^-$, $C_6F_5-SO_3^-$ and $CF_3C_6F_4-SO_3^-$.

The activated curing combinations according to the invention can be combined with cationically polymerizable organic materials to give curable compositions having the advantageous properties described above.

The invention accordingly also relates to curable compositions containing a) a cationically polymerizable organic material and
b) an activated curing combination as defined above.

The amount of curing component b) is, as a rule, 0.05–0.5 part by weight, preferably 0.15–0.3 part by weight, relative to one part by weight of the polymerizable material.

The components a) and b) are, as a rule, mixed at low temperatures, for example below 50° C., to prevent premature gelling or curing.

Examples of cationically polymerizable organic materials have been described in the abovementioned publications which deal with the polymerization of these curable materials in the presence of metallocene salts.

Curable compositions in which component a) is a cationically polymerizable cyclic ether are preferred.

The particularly preferred components a) include epoxy resins.

The invention accordingly in particular relates to curable compositions containing as component a) a compound having on average at least two 1,2-epoxy groups per molecule and component b), as defined above.

A large number of conventional epoxy resins can be used as component a). The compounds can be used by themselves or as a mixture of several epoxy resins or even in combination with other monomers which are curable by means of component b).

Examples of epoxy resins are:

I) Polyglycidyl and poly($\beta$-methylglycidyl) esters obtainable, for example, by reaction of a compound containing at least two carboxyl groups in the molecule with epichlorohydrin, glycerol dichlorohydrin or with $\beta$-methylepichlorohydrin in the presence of bases.

Examples of compounds having at least two carboxyl groups in the molecule are the polycarboxylic acids, as already described above for component ii).

II) Polyglycidyl and poly($\beta$-methylglycidyl) ethers obtainable, for example, by reaction of a compound containing at least two alcoholic hydroxyl groups and/or phenolic hydroxyl groups in the molecule with epichlorohydrin, glycerol dichlorohydrin or with $\beta$-methylepichlorohydrin under alkaline conditions or in the presence of an acid catalyst and subsequent treatment with alkali.

Examples of compounds having at least two alcoholic hydroxyl groups and/or phenolic hydroxyl groups in the molecule are aliphatic alcohols, such as ethylene glycol, diethylene glycol and higher poly(oxyethylene) glycols, propane-1,2-diol, propane-1,3-diol or higher poly(oxypropylene) glycols, butane-1,4-diol or higher poly(oxybutylene) glycols, pentane-1,5-diol, hexane-1,6-diol, octane-1,8-diol, decane-1,10-diol or dodecane-1,12-diol, hexane-2,4,6-triol, glycerol, 1,1,1-trimethylolpropane, pentaerythritol, sorbitol or polyepichlorohydrins; or cycloaliphatic alcohols, such as 1,3- or 1,4-dihydroxycyclohexane, 1,4-cyclohexanedimethanol, bis(4-hydroxycyclohexyl)methane, 2,2-bis(4-hydroxycyclohexyl)propane or 1,1-bis(hydroxymethyl)cyclohex-3-ene; or alcohols containing aromatic groups, such as N,N-bis(2-hydroxyethyl)-aniline or p,p'-bis(2-hydroxyethylamino)diphenylmethane; or mono- or polynuclear polyphenols, such as resorcinol, hydroquinone, bis(4-hydroxyphenyl)methane, 2,2-bis-(4-hydroxyphenyl)propane, brominated 2,2-bis(4-hydroxyphenyl)propane, bis(4-hydroxyphenyl) ether, bis(4-hydroxy-phenyl) sulfone, 1,1,2,2-tetrakis(4-hydroxyphenyl)ethane or novolaks obtainable by condensation of aldehydes, such as formaldehyde, acetaldehyde, chloral or furfuraldehyde with unsubstituted or alkyl- or halogen-substituted phenols, such as phenol, the bisphenols described above, 2- or 4-methylphenol, 4-tert-butylphenol, p-nonylphenol or 4-chlorophenol.

III) Poly(S-glycidyl) compounds, for example di-S-glycidyl derivatives derived from dithiols, such as ethane-1,2-dithiol or from bis(4-mercaptomethylphenyl) ether.

IV) Epoxidation products of dienes or polyenes, such as cycloaliphatic epoxy resins preparable, for example, by epoxidation of ethylenically unsaturated cycloaliphatic compounds. Examples of these are 1,2-bis(2,3-epoxycyclopentyloxy)ethane, 2,3-epoxycyclopentylglycidyl ether, bis(2,3-epoxycyclopentyl) ether, 5(6)-glycidyl-2-(1,2-epoxyethyl)bicyclo[2.2.1]-heptane, dicyclopentadiene dioxide, 3,4-epoxy-6-methylcyclohexylmethyl-3',4'-epoxy-6'-methylcyclohexanecarboxylate or 3,4-epoxycyclohexylmethyl-3', 4'-epoxycyclohexanecarboxylate.

However, it is also possible to use epoxy resins in which the 1,2-epoxy group is bound to different heteroatoms or functional groups; this type of compound includes, for example, the glycidyl ether/glycidyl ester of salicylic acid.

Very particular preference is given to curable mixtures containing a) a cycloaliphatic epoxy resin, in particular one containing two 1,2-epoxy groups and
b) an activated curing combination as defined above and derived from a compound of the formula I and a polyisocyanate.

Mixtures of this type are distinguished by a particularly long shelf life at room temperature.

The curable compositions according to the invention can be obtained in any desired form, for example as homogeneous liquid or solid mixtures. These compositions, in contrast to curable compositions containing iron/arene initiators, are in general no longer radiation-sensitive. They can be cured directly by heat, and the curing temperatures are in general considerably less than those of previously known compositions.

The preferably liquid activated curing component can be mixed into the cationically polymerizable material by conventional means, such as stirrers, rolls or kneaders, and preferably at temperatures below 50° C.

The curing is preferably carried out below 200° C., in particular in the range from 50° to 180° C. It is, however, also possible to carry out precuring at lower temperatures until the curable composition becomes a gel, followed by curing at higher temperatures.

The cured products are distinguished by good mechanical and electrical properties when finished; in particular the small degree of embrittlement of the final products must be considered surprising.

Furthermore, high throughputs can be achieved in the curing, in particular with machine-processed products, since rapid gelling at low temperatures is possible and also the postcuring times at elevated temperature can be kept short. In the processing of the curable compositions according to the invention it must be considered a further advantage that the mixing ratio of components a) to b) is in general not critical for the curing conditions. Thus, this mixing ratio can be varied especially in machine-processed products without having to adapt the curing conditions each time.

The invention accordingly also relates to a process for the preparation of cured products, which comprises curing a curable composition according to the invention by heating; furthermore, the invention relates to the cured products obtainable by heating the curable composition according to the invention.

If desired, reactive thinners, for example styrene oxide, butyl glycidyl ether, 2,2,4-trimethylpentyl glycidyl ether, phenyl glycidyl ether, cresyl glycidyl ether or glycidyl esters of synthetic, highly branched, mainly tertiary aliphatic monocarboxylic acids, can be added to the curable compositions to reduce the viscosity.

Furthermore, the compositions according to the invention can contain further customary additives such as plasticizers, extenders, fillers and reinforcing agents, for example coal tar, bitumen, textile fibres, glass fibres, asbestos fibres, boron fibres, carbon fibres, mineral silicates, mica, ground quartz, hydrated alumina, bentonites, wollastonite, kaolin, silica aerogel or metal powder, for example aluminium powder or iron powder, furthermore pigments and dyes, such as carbon black, oxide paints and titanium dioxide, and flame retardants, antifoams, thixotropic agents, flow-improving agents (some of which can also be used as mould release agents), such as silicones, waxes and stearates, or adhesives, antioxidants and light stabilizers.

The amount of additives is usually 0–85 parts by weight, relative to 100 parts by weight of the curable composition.

Very generally, the curable compositions according to the invention can be used for the preparation of cured products and can be used in the formulation adapted to the particular specific area of application, for example as coating materials, paints, moulding compounds, dipping resins, casting resins, impregnating resins, laminating resins, adhesives or matrix resins.

The curable compositions according to the invention can in particular be used as encapsulating or sheathing material for electronic components, for the manufacture of insulating structural supports or as one-component adhesive.

The invention also relates to the use of the curable mixtures for the abovementioned purposes.

The examples which follow illustrate the invention:

I. Preparation of the curing components

I.1. Curing component A: A solution consisting of 162 g of methyltetrahydrophthalic anhydride (Hitachi HN 2200), 38 g of a reaction product from 2 equivalents of tetrahydrophthalic anhydride and 1 equivalent of 2,2-dimethylpropanediol and 1 g of ($\eta^6$-cumene)($\eta^5$-cyclopentadienyl)iron(II) hexafluoroantimonate are irradiated in a 250 ml photoreactor through a Pyrex immersion tube by means of a 125W mercury high-pressure lamp under an argon atmosphere with stirring at room temperature for 1.5 hours. This gives a dark brown clear solution. I.2. Curing component B: A solution consisting of 162 g of methyltetrahydrophthalic anhydride (Hitachi HN 2200), 38 g of a reaction product from 2 equivalents of tetrahydrophthalic anhydride and 1 equivalent of 2,2-dimethylpropanediol and 1 g of ($\eta^6$-1-methylnaphthalene)($\eta^5$-cyclopentadienyl)iron(II) hexafluoroantimonate are heated in a 500 ml roundbottomed flask under an argon atmosphere at 140° C. for 1 hour. After cooling to room temperature, a dark brown clear solution is obtained. I.3. Curing component C: A solution consisting of 100 g of methylhexahydrophthalic anhydride and 1 g of ($\eta^6$-cumene)($\eta^5$-cyclopentadienyl)iron(II) hexafluoroantimonate are irradiated in a 250 ml photoreactor through a Pyrex immersion tube by means of a 125W mercury high-pressure lamp under an argon atmosphere with stirring at room temperature for 1.5 hours. This gives a dark brown clear solution.

I.4. Curing component D: 60.4 g of bis($\eta^6$-mesitylene)iron(II) hexafluoroantimonate are finely powdered and dispersed in 205 g of methylhexahydrophthalic anhydride. The dispersion is degassed by means of argon, made inert and heated to 120° C. with stirring. After 45 minutes a clear dark brown solution has formed, which is freed from volatile components at 120° C. in vacuo (0.1 mbar) for 15 minutes. This gives 246.1 g of a viscous brown liquid. A portion of this product is dissolved in 30 parts of methylhexahydrophthalic anhydride to give the curing component D. I.5. Curing component E: A solution consisting of 100 g isophorone diisocyanate (IPDI) and 5 g of ($\eta^6$-cumene)($\eta^5$-cyclopentadienyl)-iron-II-hexafluoroantimonate is irradiated in a 250 ml photoreactor through a Pyrex immersion tube by means of a 125W mercury high pressure lamp under an argon atmosphere with stirring at room temperature for 1.5 hours. This gives a light brown clear solution.

II. Working examples

II.1. Example A: 100 g of a technical grade bisphenol A diglycidyl ether (epoxy value: 5.2 equivalents/kg) and 25 g of curing component A from Example I.1. are mixed at room temperature in an aluminium mould and then heated at 180° C. for two hours. This gives a dark brown moulded article which has a glass transition temperature of 131° C. (measured in a DSC experiment).

II.2. Example B: 70 g of a technical grade bisphenol A diglycidyl ether (epoxy value: 5.2 equivalents/kg), 30 g of 3,4-epoxycyclohexylmethyl 3',4'-epoxycyclohexanecarboxylate, 25 g of curing component B from Example I.2. are mixed at room temperature in an aluminium mould and then heated at 180° C. for two hours. This gives a dark brown moulded article which has a glass transition temperature of 149° C. (measured in a DSC experiment).

II.3. Example C: 70 g of a technical grade bisphenol A diglycidyl ether (epoxy value: 5.2 equivalents/kg), 30 g of 3,4-epoxycyclohexylmethyl 3',4'-epoxycyclohexanecarboxylate, 25 g of curing component A from Example I.1. and 200 g of ground quartz (Novacite 1250) are mixed at room temperature in an aluminium mould and then heated at 180° C. for two hours. This gives a dark brown moulded article which has a glass transition temperature of 154° C. (measured in a DSC experiment) and a linear coefficient of thermal expansion of $40 \times 10^{-6}$ [°C.$^{-1}$] at 80° C.

II.4. Example D: 70 g of a technical grade bisphenol A diglycidyl ether (epoxy value: 5.2 equivalents/kg), 30 g of 3,4-epoxycyclohexylmethyl 3',4'-epoxycyclohexanecarboxylate and 25 g of curing component C from Example I.3. are mixed at room temperature in an aluminium mould and then heated at 180° C. for two hours. This gives a dark brown moulded article which has a glass transition temperature of 185° C. (measured in a DSC experiment).

II.5. Example E: 100 g of a bisphenol A diglycidyl ether (epoxy value: 5.2 equivalents/kg) and 25 g of curing component D from Example I.4. are mixed at room temperature in an aluminium mould and then heated at 130° C. for 2 hours and 180° C. for 4 hours. This gives a dark moulded article which has a glass transition temperature of 159° C. (measured by DSC).

II 6. Example F: 100 g of 3,4-epoxicyclohexylmethyl-3',4'-epoxicyclohexanecarboxylate and 25 g of curing component E according to Example I.5. are mixed at room temperature in an aluminium mould and then heated for 0.5 hours at 130° C. and then for 4 hours at 180° C. This gives a dark brown moulded article which has a glass transition temperature of 147° C. (measured in a DSC experiment).

What is claimed is:

1. A composition of matter obtainable by
   A) dissolving or dispersing a component i) in a component ii), component i) being a compound of the formula I

   $$[(R^1)(R^2Fe^{II})_a]^{+na}{}_{na} X^- \quad (I)$$

and component ii) being selected from the group consisting of a polycarboxylic acid, an anhydride based on a polycarboxylic acid, or a polyisocyanate, in which, in formula I, $R^1$ is a π-arene, $R^2$ is a π-arene or an anion of a π-arene, a and n, independently of one another, are 1 or 2, and X is an anion $[LQ_m]^-$ or an anion of an unfluorinated, partially fluorinated or perfluorinated aliphatic, cycloaliphatic, aromatic or araliphatic carboxylic acid or sulfonic acid, in which L is selected from the group consisting of B, P, As, Sb and Bi, Q is a halogen atom and m corresponds to the valency of L increased by one, and
   B) activating said solution or dispersion containing components i) and ii) by irradiation with actinic radiation or by heating, so that component i) is virtually no longer detectable in said solution or dispersion.

2. A composition of matter according to claim 1, in which $R^1$ or $R^2$ are carbocyclic-aromatic hydrocarbons having 6–24 C atoms in the aromatic ring, or heterocyclic-aromatic hydrocarbons having 4–11 C atoms and 1 or 2 O atoms or S atoms in the aromatic ring.

3. A composition of matter according to claim 1, in which $R^2$ is a cyclopentadienyl anion.

4. A composition of matter according to claim 1, in which $X^-$ is $PF_6^-$, $AsF_6^-$, $SbF_6^-$, $BiF_6^-$ or an anion of perfluoroaliphatic or perfluoroaromatic sulfonic acids.

5. A composition of matter according to claim 1, in which component ii) is a polyisocyanate.

6. A composition of matter according to claim 1, in which component ii) is an anhydride of a polycarboxylic acid or a mixture of this type of anhydride.

7. A composition of matter according to claim 6, in which component ii) is liquid at temperatures below 50° C.

8. A composition of matter according to claim 1, in which components i) and ii) and their amounts are chosen such that a solution can be prepared from these components.

9. A composition of matter according to claim 1, obtainable by
   A) dissolving component i) in a combination of component ii) with a further component iii) and
   B) activating this solution according to claim 1, in which component i) is as defined in claim 1, component ii) is an anhydride of a polycarboxylic acid and component iii) is a polycarboxylic acid or a carboxylterminated adduct of a polycarboxylic acid or one of its ester-forming derivatives to an at least dihydric alcohol and/or an at least dihydric phenol.

10. A composition of matter according to claim 1, in which the compounds used as component i) are those of the formula I in which a and n are 1, $R^1$ is a benzene or naphthalene radical which is unsubstituted or mono-or disubstituted by $C_1$-$C_4$alkyl or $C_1$-$C_4$alkoxy or is a stilbene radical, $R^2$ is an unsubstituted cyclopentadienyl anion and $X^-$ is an anion selected from the group consisting of $PF_6^-$, $AsF_6^-$, $SbF_6^-$, $BiF_6^-$ and of anions of perfluoroaliphatic or perfluoroaromatic sulfonic acids, in particular $CF_3-SO_3^-$, $C_2F_5-SO_3^-$, $C_3F_7-SO_3^-$, $C_4F_9-SO_3^-$, $C_6F_{13}-SO_3^-$, $C_8F_{17}-SO_3^-$, $C_6F_5-SO_3^-$ and $CF_3-C_6F_4-SO_3^-$.

11. A curable composition containing
    a) a cationically polymericable organic material and
    b) an activated curing combination according to claim 1.

12. A curable composition according to claim 11, in which component a) is a compound having on average at least two 1,2-epoxy groups per molecule.

13. A curable composition according to claim 11, in which component a) is a cycloaliphatic epoxy resin and where in component $b)_2$ component ii) is a polyisocyanate.

14. A cured product obtainable by heating a curable composition according to claim 11.

15. A cured product according to claim 14, in which the curable composition contains as component a) a compound having on average 16. A cured product according to claim 14, in which the curable composition contains as component a) a cycloaliphatic epoxy resin and where in component b), component ii) is a polyiocyanate.

17. A composition of matter according to claim 1 in which the weight ratios of components i) and ii) or of component i) and components ii)+iii) in the starting mixture are 0.5:100 to 5:100.

18. A composition of matter according to claim 9 in which the weight ratios of components i) and ii) or of component i) and components ii)+iii) in the starting mixture are 0.5:100 to 5:100.

* * * * *